United States Patent
Hadváry et al.

(10) Patent No.: US 8,224,410 B2
(45) Date of Patent: Jul. 17, 2012

(54) DERMALLY AFFIXED SENSOR DEVICE

(76) Inventors: Paul Hadváry, Biel-Benken (CH);
Tschirky Hansjörg, Ettingen (CH)

(*) Notice: Subject to any disclaimer, the term of this patent is extended or adjusted under 35 U.S.C. 154(b) by 1466 days.

(21) Appl. No.: 10/586,925

(22) PCT Filed: Dec. 10, 2004

(86) PCT No.: PCT/EP2004/014057
§ 371 (c)(1),
(2), (4) Date: Apr. 12, 2007

(87) PCT Pub. No.: WO2005/063115
PCT Pub. Date: Jul. 14, 2005

(65) Prior Publication Data
US 2008/0027296 A1   Jan. 31, 2008

(30) Foreign Application Priority Data
Dec. 22, 2003 (EP) .................................. 03029565

(51) Int. Cl.
*A61B 5/1455* (2006.01)
(52) U.S. Cl. .................. 600/310; 600/316; 600/322
(58) Field of Classification Search .................. 600/309, 600/310, 322, 345–356; 604/131, 132
See application file for complete search history.

(56) References Cited

U.S. PATENT DOCUMENTS

| | | | | |
|---|---|---|---|---|
| 4,953,552 A | * | 9/1990 | DeMarzo | 600/347 |
| 5,353,792 A | * | 10/1994 | Lubbers et al. | 600/311 |
| 5,746,217 A | * | 5/1998 | Erickson et al. | 600/310 |
| 5,931,814 A | * | 8/1999 | Alex et al. | 604/131 |
| 6,058,321 A | * | 5/2000 | Swayze et al. | 600/310 |
| 6,186,982 B1 | * | 2/2001 | Gross et al. | 604/132 |
| 6,275,717 B1 | | 8/2001 | Gross et al. | |
| 6,537,242 B1 | * | 3/2003 | Palmer | 600/309 |
| 6,584,335 B1 | * | 6/2003 | Haar et al. | 600/322 |
| 2002/0137998 A1 | | 9/2002 | Smart et al. | |

FOREIGN PATENT DOCUMENTS

EP   0 789 540 A   8/1997
WO   WO 03/037403 A   5/2003

OTHER PUBLICATIONS

International Application dated Mar. 15, 2005 for International Application No. PCT/EP2004/014057.

* cited by examiner

*Primary Examiner* — Eric Winakur
*Assistant Examiner* — Chu Chuan (JJ) Liu
(74) *Attorney, Agent, or Firm* — Hogan Lovells US LLP

(57) ABSTRACT

An improved diagnostic analyte monitoring device has immovable, rigid sensors connected stationarily to control and measuring means and a flexible surface adhering to the skin and serving for the subcutaneous implantation of the sensors, actuated by means designed for easy handling. Concentration time profiles of endogenous and exogenous analytes measured with the device are used to improve drug treatment modalities on an individualized basis.

26 Claims, 12 Drawing Sheets

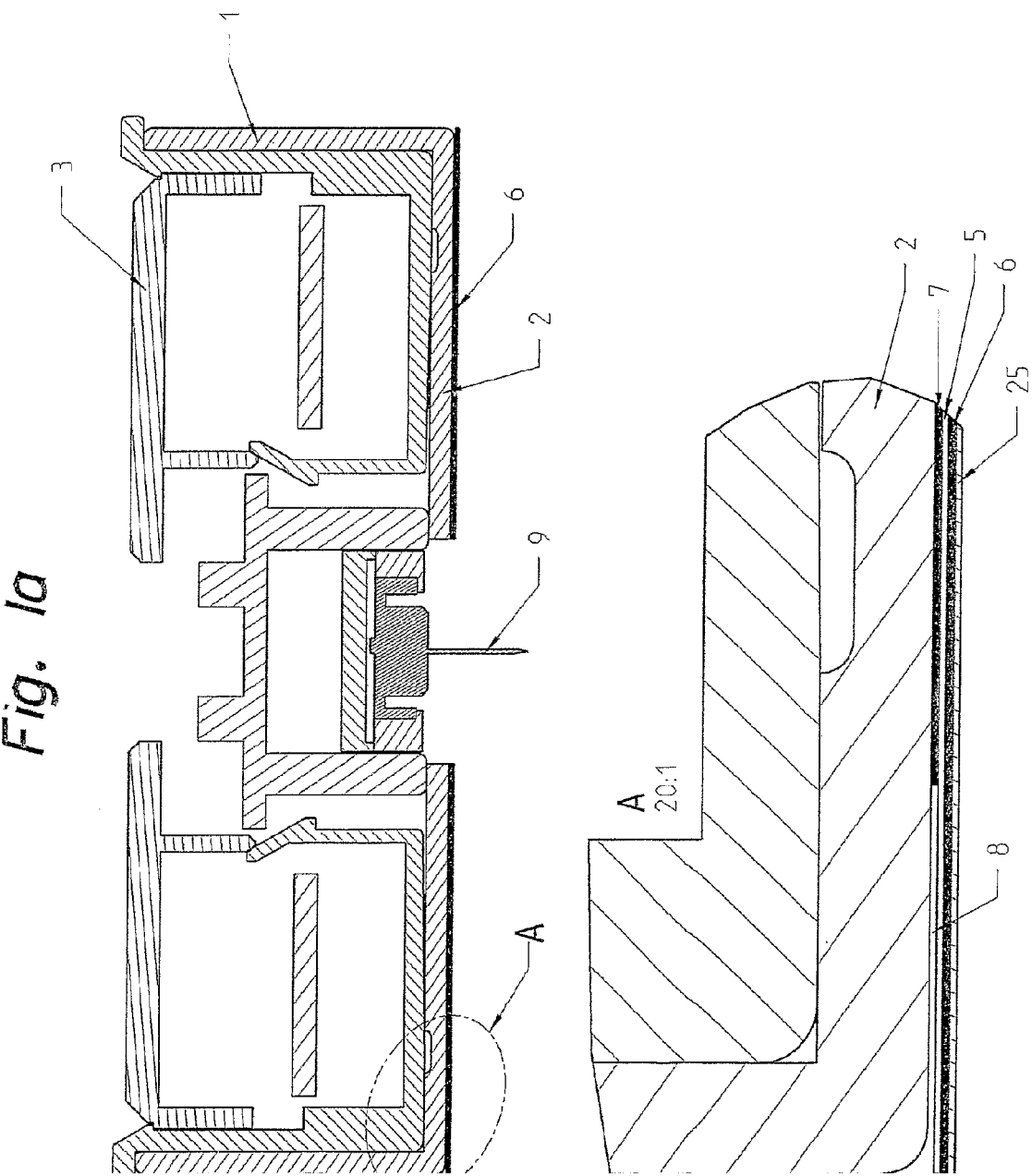

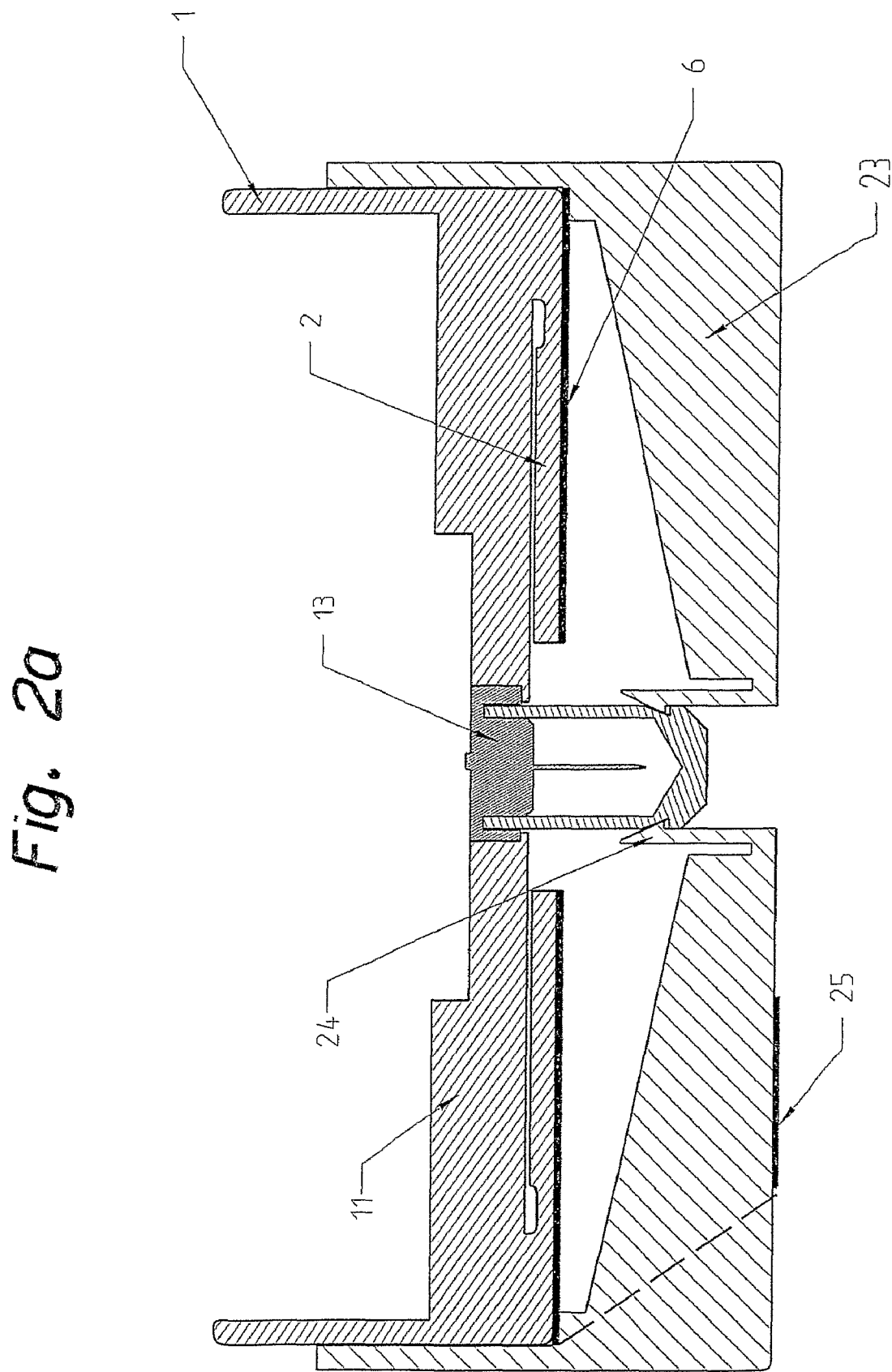

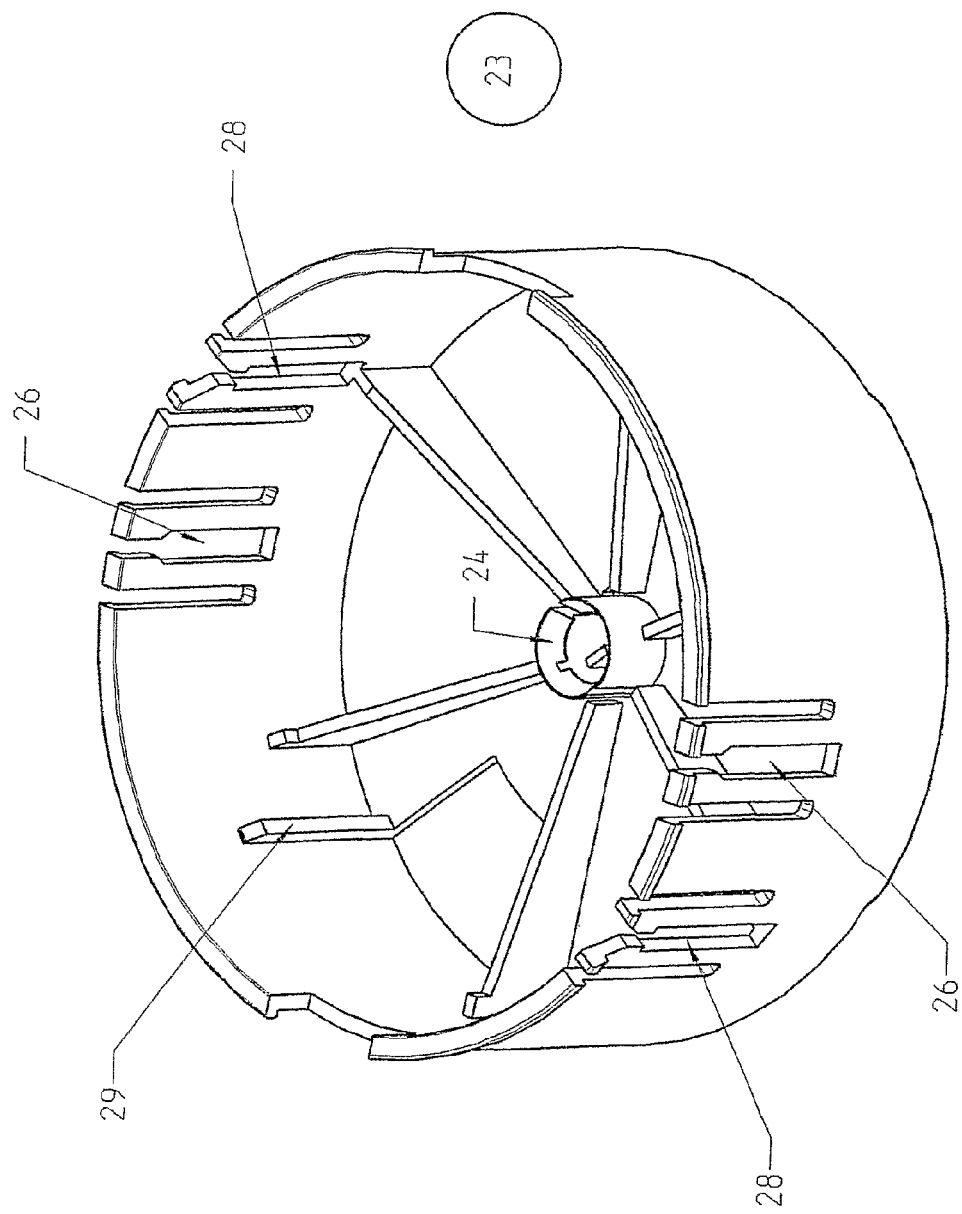

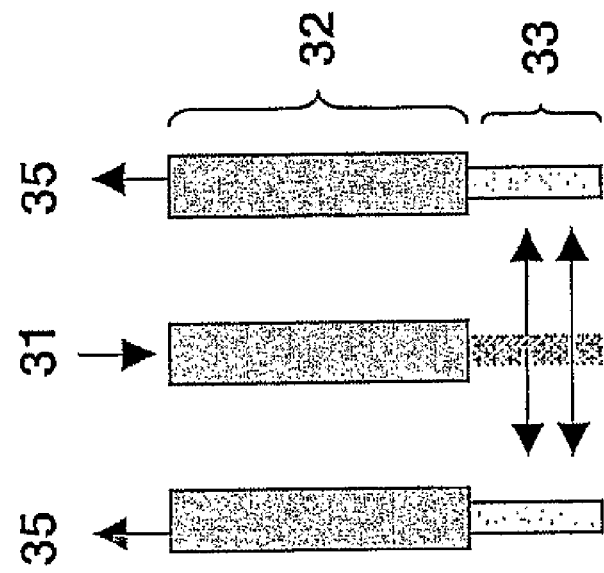
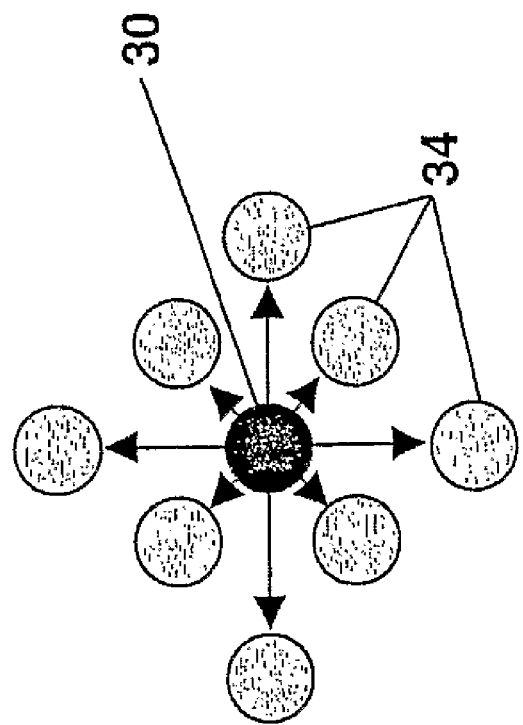
Fig. 4g

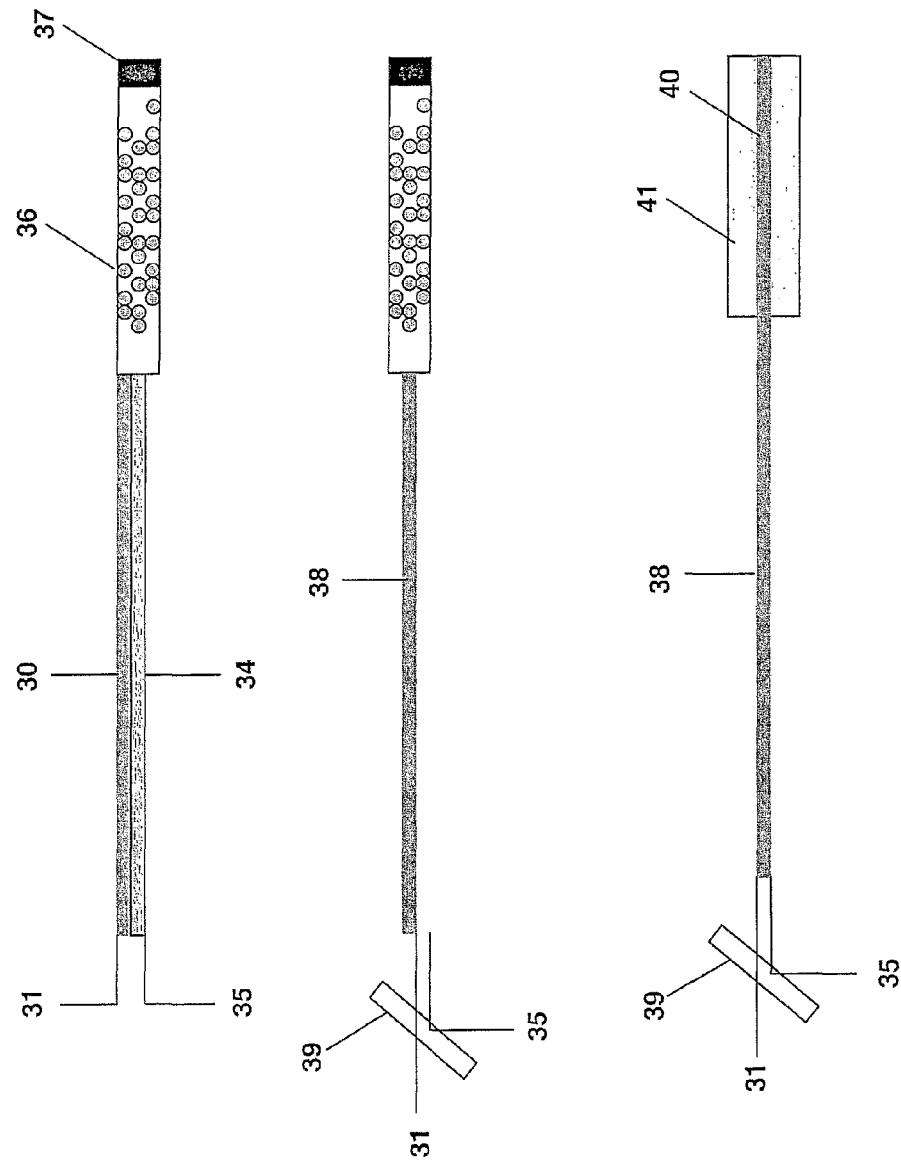

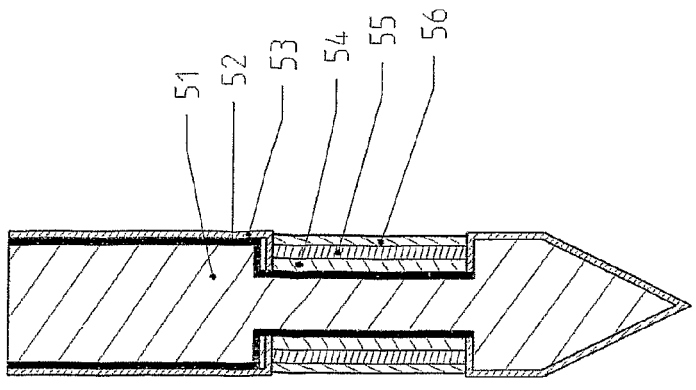
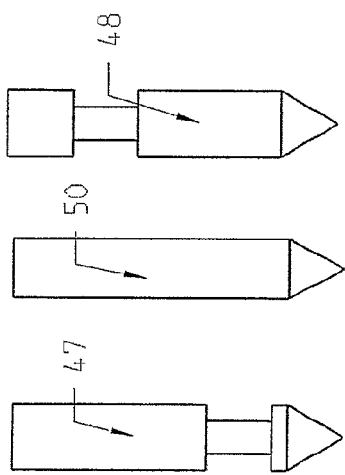
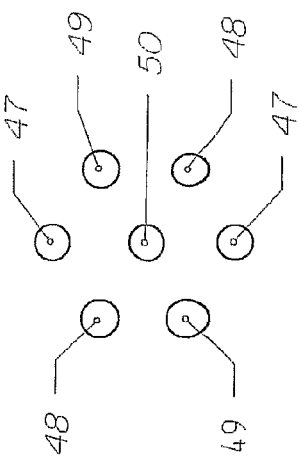

DERMALLY AFFIXED SENSOR DEVICE

FIELD OF THE INVENTION

The invention relates generally to analytical devices and methods which allow to monitor the concentration of an analyte using a subcutaneous sensor.

BACKGROUND OF THE INVENTION

The monitoring of the level of endogenous analytes such as glucose, lactate, creatinine or oxygen, in certain individuals, is vitally important for their health. Certain substances such as glucose can also be administered for diagnostic stress-tests. In addition, monitoring of the level of xenobiotics such as inulin, and certain drugs and their metabolites is important for diagnosis of e.g. kidney and liver function and can be vitally important for the choice and correct dosing in drug treatment. For a chosen drug, monitoring of its pharmacokinetics under treatment conditions in a given patient can allow individualized optimization of treatment schedule and help to avoid potentially serious drug-drug interactions. For such applications a reliable device which allows monitoring of analyte concentration in body fluids such as e.g. subcutaneous interstitial fluid for several hours to a few days is necessary. To achieve acceptance from patients and non-specialized health care professionals, convenience and minimal invasiveness are extremely important features.

A convenient alternative to frequent blood sampling is to measure the concentration of the analyte in dermal interstitial fluid since the concentration of certain analytes such as e.g. glucose is highly correlated between these two fluid compartments (Bantle, et al., J Lab Clin Med 1997; 130: 436-441). Sensors for e.g. glucose monitoring in interstitial fluid are known in the art, for example U.S. Pat. No. 6,579,690, published Jun. 17, 2003 by Bonnecaze et al. Bonnecaze et al describe various embodiments of such sensor devices. One important feature of these devices as well as of devices prior in the art is that the sensor is first implanted into the body and in a second step, on the patient, has to be connected to a control unit. Such a procedure especially with miniaturized components needs a high level of skill and the use of mounting tools is complicated. These drawbacks severely limit the acceptance and can easily lead to incorrect functioning. Fully implantable sensors including wireless transmitters avoid the problems of mounting together the several components after implantation of the sensor. On the other hand, their size necessitates a surgical procedure for implantation with the associated inconveniences for the patient and needs qualified health care professionals for the implantation. The damage inflicted on the subcutaneous tissue upon implantation of the sensor results in inflammatory tissue reactions which can alter the performance of the sensor and even lead to changes in the availability of analytes surrounding the sensor. Therefore, for reliable measurements, minimal invasiveness is very important. This can only be achieved by miniaturization of the implanted parts of the sensor and optimization of the sensor shape and insertion means to avoid tissue damage upon insertion as much as possible. The sensors and insertion mechanisms of prior art are far from optimal in this respect.

To circumvent the inherent handling problems with implantable sensors, several approaches were taken to withdraw subcutaneous fluid by making holes into the skin by lancing or with a laser beam, or to withdraw fluid with an electric current. Since the volume which can be withdrawn by these means is very small, usually below 1 µl, the determination of analyte concentrations is technically difficult and not reliable and many factors, e.g. sweating can lead to changes of the composition and to massively wrong determinations.

SUMMARY OF THE INVENTION

The subject invention overcomes the problems with current subcutaneous sensors by incorporating tailored functional elements such as sensor, implantation means and control and measuring means into one single device unit which is attached to the skin of the patient. The subject invention allows for a construction circumventing the need to move the sensors relative to all the other elements included in the device. This allows in particular for a rigid connection between the sensors and the analyte monitoring/control system resulting in much simpler construction and higher reliability for performance than flexible connections. Assembly of the entire system including all connections and setting it into a ready-to-use state is done before placing the device on the skin of the patient and all functional procedures such as adhesion to the skin, implantation of the sensor and start of the measurements can be accomplished with one single and easy manipulation step, such as pressing a release button. The construction allows also for an unprecedented miniaturization and optimization of the design of the implanted part of the sensors, thus becoming minimally invasive and therewith painless and of high reliability. In addition, the device of the subject invention can accommodate many different types of sensors in an optimal way.

More particularly the invention relates to a device for the in-vivo measurement of the concentration of an analyte in a body fluid comprising a) a component with a flexible surface, b) means for securing adherence of that surface to the skin, c) a rigid part holding one or more subcutaneously implantable sensors, d) means to position the flexible surface relative to the sensors in such a way that in a first position the sensors are concealed by the surface and in a second position the implantable parts of the sensors are exposed above the surface, and e) a mechanism to bring the surface from one to the other position. The invention further relates to methods for the measurement of the concentration-time profiles of endogenous and exogenous substances and the use of these methods for automatic dose adjustments.

DEFINITIONS

When used herein, the following definitions define the stated term

Analyte means any endogenous or exogenous substance the concentration of which can be used to diagnose the health, organ function, metabolic status, or drug metabolizing capacity of an individual or of an animal. Examples of endogenous substances are glucose, lactate, oxygen, creatinine, etc. Examples of exogenous substances are drugs, metabolites of such drugs, diagnostic substances (e.g. inulin) etc.

Body fluid is interstitial fluid or blood.

Component with a flexible surface is made up of a casing which is preferentially cylindrical and which has a flexible base. This base plate is constructed in such a way that it can be deformed to a convex shape (position 1) with the central part protruding e.g. like a cone. An additional feature of this base is that it can shoot from the convex shape into a flat shape (position 2) with sufficient velocity and force that this movement can provide the driving energy for implantation of the sensors. Such a flexible surface can be constructed by appropriate segmentation of the surface with hinge regions acting like springs and/or by using materials with the necessary reversible stretching characteristics. Such a component with a flexible surface can be manufactured by injection moulding of suitable plastics but also by using other materials like steel, composite or ceramic materials, etc. The base of this element has a hole, preferentially in the center, as opening for the implantable part of the sensors. The sensors are positioned axially to this base in such a way that in position 1 they are entirely covered up, whereas in position 2 they protrude above the base.

Means securing adherence to the skin is an adhesive layer for temporary wearing on the body made of materials with strong adhesive properties, stretchability and minimal allergenicity. This adhesive layer is fixed on the flexible base of the device in such a way that it does not interfere with its flexibility. Preferentially the surface of the adhesive layer which is fixed to the skin is larger than its surface which is fixed to the flexible base of the device. This can be accomplished e.g. by an adhesive layer extending beyond the surface of the base of the device or, preferentially by using a shape for the adhesive surface to the skin similar to the surface of the flexible surface of the device but fixing it to the latter in such a way that an outer annular zone is not fixed to the base of the device.

A rigid part holding one or more subcutaneously implantable sensors is constructed in such a way that it forms a bridge to the casing of the component with the flexible surface and allows a firm and rigid attachment to the casing holding the non-implanted parts of the sensors and the control and measuring means. In particular, in the case that the device can be assembled using a disposable and a reusable part, it allows the correct electrical and/or optical coupling between the implantable, single-use parts of the sensors and their reusable measuring means. In addition, it contains means such as recognition codes for the logical coupling between the disposable and reusable part of the device, relevant for correct functioning of the control and measuring means. The implantable parts of the sensors are hold in such a way that they are fixed in an axial geometry relative to the flexible surface and in a well defined geometry relative to each other, allowing well defined sterical conditions for optimal performance even if several implantable sensor elements are used together for measurements, as described later. In addition, this rigid part can hold a removable cap to protect the implantable parts of the sensors during storage in a defined environment, such as humidity and allows maintaining sterility.

Means to position the flexible surface relative to the sensors in two defined positions consists of elements which can bring about the deformation of the flexible surface to a convex, pre-stressed shape (position 1) and allow a rapid release from this position to adopt a flat, relaxed shape (position 2) in a coordinated way for the entire surface. This can be accomplished preferentially by several pin-shaped elements protruding from a central pressure plate and pushing onto the flexible surface, but other constructions using screws, ramps, levers etc. are also possible.

A mechanisms to bring the surface from one to the other position, in a first step, transmits the energy and movement needed for deformation of the flexible surface, such as a manual pressure or torsion, to the means to position the flexible surface described above. This can be a knob pressing on a pressure plate, an element which can be turned and pushes ramps or actuates screws or other constructional elements. When the predefined position 1 of the flexible surface is reached, this mechanism results automatically in the fixation of this pre-stressed position e.g. by a catch mechanism. In the next step, upon an easy manipulation, e.g. by pressing a button or a minimal turning movement, the fixation to the pre-stressed position 1 of the flexible surface gets released and the mechanism allows for an immediate relaxation to position 2.

The sensor consists of a non-implantable part and an implantable part which is a rigid, full, thin needle shaped device, preferentially a pin coated with a sensing layer and which can be inserted into the skin in a minimally invasive and painless way. This can be achieved if the diameter of this implantable part is very small, preferentially below 0.3 mm, preferably 0.1 to 0.2 mm and has a pointed tip. The pin can have several forms, such as a sectional area of a circle, oval or polygonal. It has a hard core of steel, gold or other metals, or alternatively of glass, carbon, modified glassy carbon, or other fibers, fused silica or composite materials. The surface can be coated with noble metal, polymers or other composite materials. The pin contains a sensing layer at its surface which provides some signal (e.g. electrochemical or optic) according to the concentration of the analyte, or forms part of an electrochemical or optical system. The surface of the pin can be smooth or modeled in such a way that the sensing layer is mechanically protected from stripping when penetrating the skin e.g. by the application of impressions or grooves. In addition, the surface can be increased by an appropriate geometry to increase the signal generated by the sensing layer.

A variety of methods for the composition and structuring of suitable sensing layers has been described in the literature. These include also methods which prevent the leakage of components of the sensing layer while implanted into the skin and at the same time allow the diffusion of the analytes of interest e.g. by the use of suitable biocompatible polymers or by coating with semi-permeable membranes.

In the case of electrochemical sensors the pins are constructed as electrodes selective for the chosen analyte e.g. glucose. In the case of optical sensors the pins are constructed as optical fibers and can contain also elements for the selective optical detection of analytes in form of suitable coating and sensing layers and/or measurement chambers. In the case of thermometric, piezoelectric or magnetic sensors, the pins are constructed in such a way that they can transduce the respective signal in an optimal way.

An additional advantage of the present invention is that by the exact positioning of the implanted part of the sensors relative to each other, arrays of pins can be constructed in such a way that they form parts of one measuring system such as working electrode and counter electrode, or light source and light collector.

BRIEF DESCRIPTION OF THE FIGURES

An exemplified embodiment of the invention and several examples of sensors will now be described with reference to the accompanying drawings in which FIG. 1 is a diagrammatic representation of a device for diagnostic analyte monitoring according to one embodiment of the invention. FIG. 1*a* shows the sectional view of the device in operation mode and FIG. 1*b* is an explosion drawing depicting the flexible base plate in the pre-stressed position, for better clarity.

FIG. 2 is a diagrammatic representation of one embodiment of the device composed of a reusable and a disposable part with a tool for assembly, ready-to-use preparation and disassembly of the device. FIG. 2*a* shows a sectional view of the disposable part of the device, in a disposable mounting tool. FIG. 2*b* shows the mounting tool in a 3D representation.

FIG. 3 is a diagrammatic representation of the handling operations using the mounting tool.

FIG. 4 is a schematic representation of different embodiments for optical sensors. FIG. 4a shows a horizontal and an axial cross section of the light-emitting and light assembling fibers. FIG. 4b shows examples of optical arrangements to follow changes in the concentration of analytes and FIG. 4c shows an optical sensor based on the use of immobilized binding molecules.

FIG. 5 is a diagrammatic view of one example for a sensor array for glucose monitoring comprising 7 electrodes for subcutaneous implantation. FIG. 5a is a cross section showing the positioning of the electrodes relative to each-other, FIG. 5b is an axial cross section and FIG. 5c shows a schematic drawing of one electrode with the sensing layer for glucose.

DETAILED DESCRIPTION OF THE PREFERRED EMBODIMENT

The invention will now be described in terms of its preferred embodiment. This embodiment is set forth to aid in the understanding of the invention, but is not to be construed as limiting.

The exemplified embodiment is described with reference to the drawings. This embodiment is a diagnostic device which can be worn and operated by the patient. One aim of the present invention is to insert the sensors into the skin of a patient substantially without pain, thus avoiding the natural reluctance of the patient to invasive procedures and to reduce the reactions of the body to injury to a minimum. Another aim is to maintain an exact positioning of the implanted parts of the sensors relative to the device, to the skin and to each other leading to measurements with improved reliability. Further, immovable connections between the implantable part of the sensors and the measuring equipment, which becomes possible according to the present invention, greatly improves the reliability of the sensors and makes the constructions much simpler. In addition, the necessary handling by the patient is reduced to a minimum of easy manipulations, like the pressing of a knob, which do not require nimble fingers for implanting the sensors and/or making the connections to the control and measuring instruments.

Figure 1B:
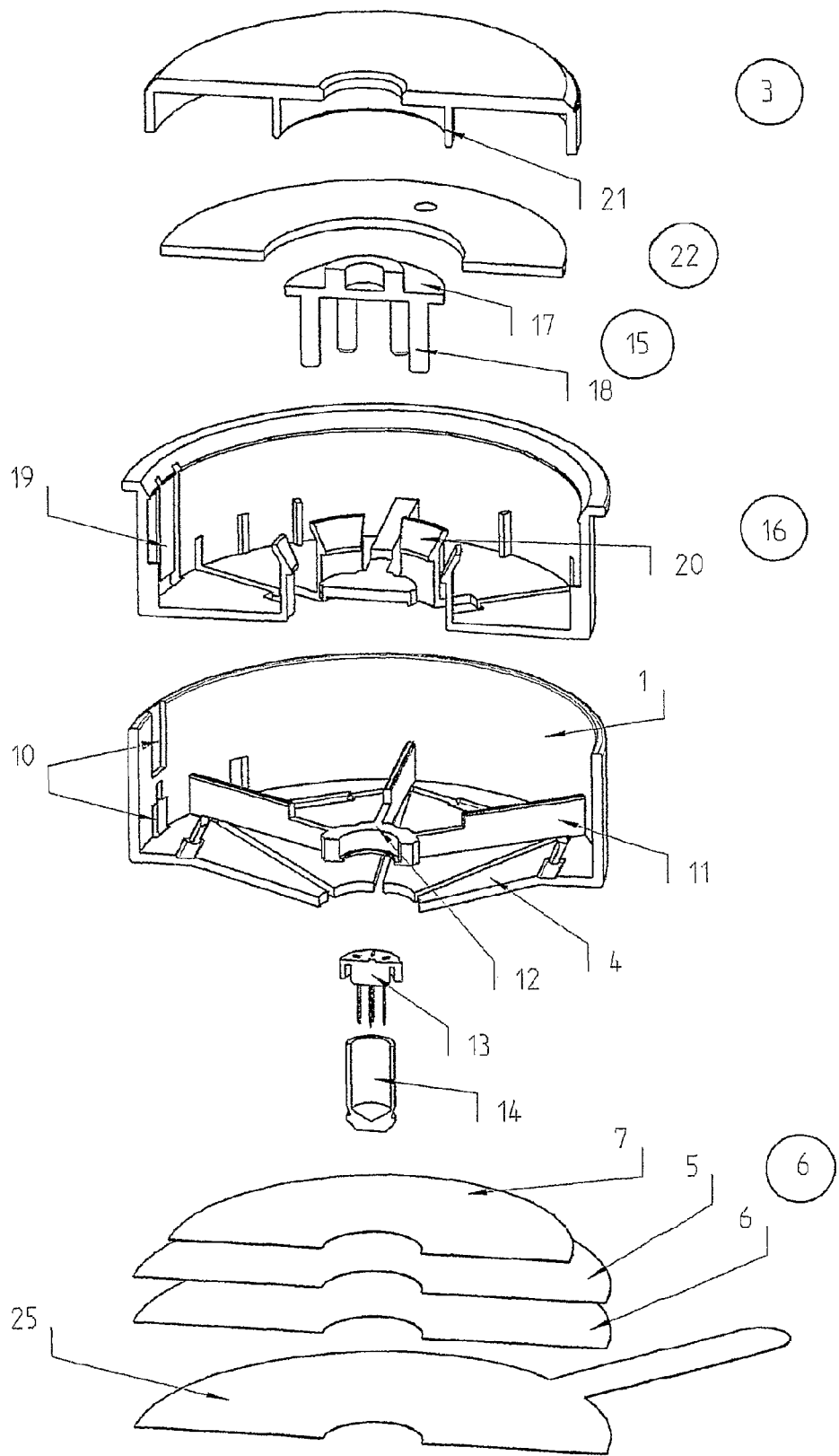
Figure 3A:
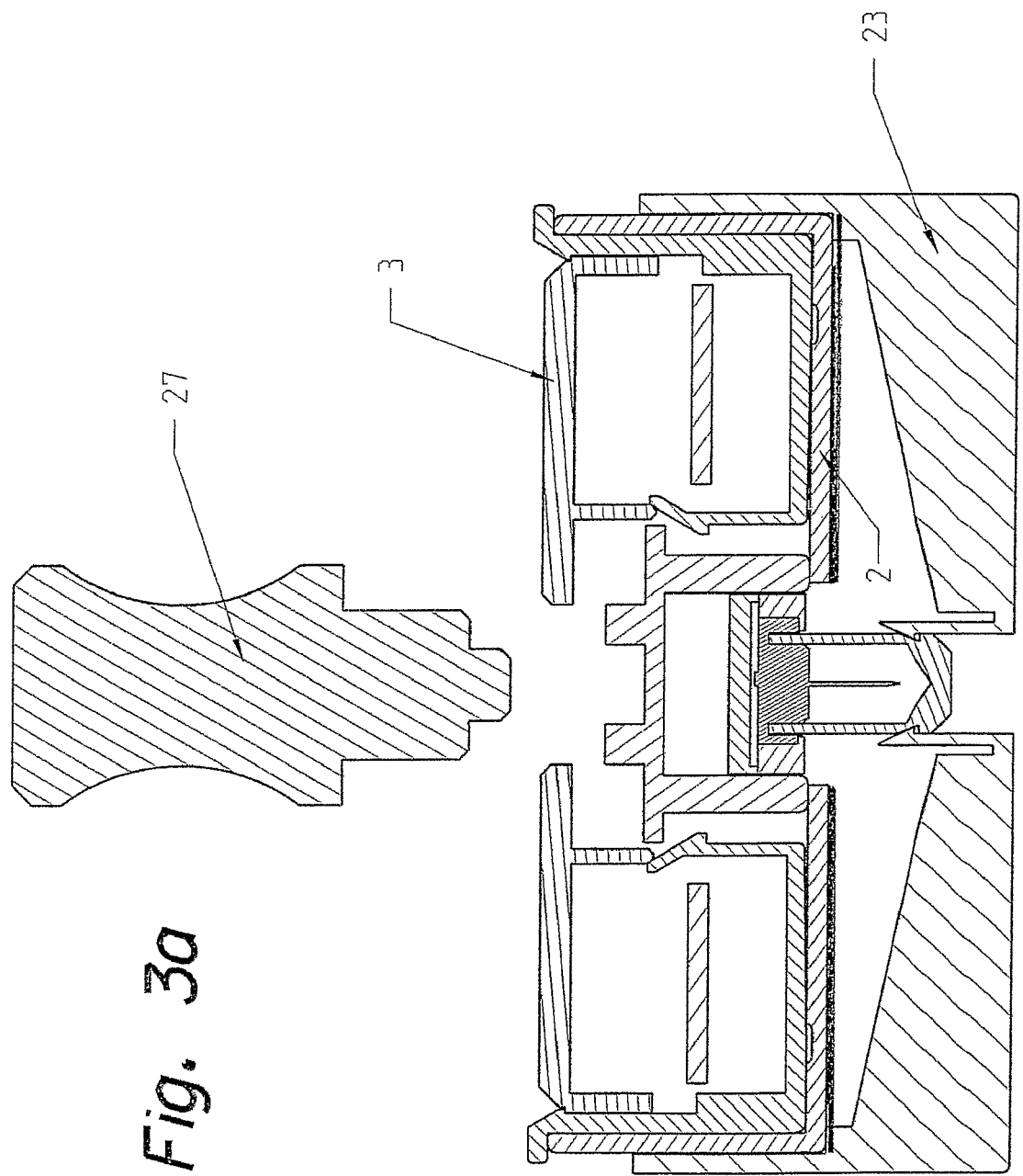
FIG. 3*a* shows the assembled reusable and disposable parts in the tool.
Figure 3B:
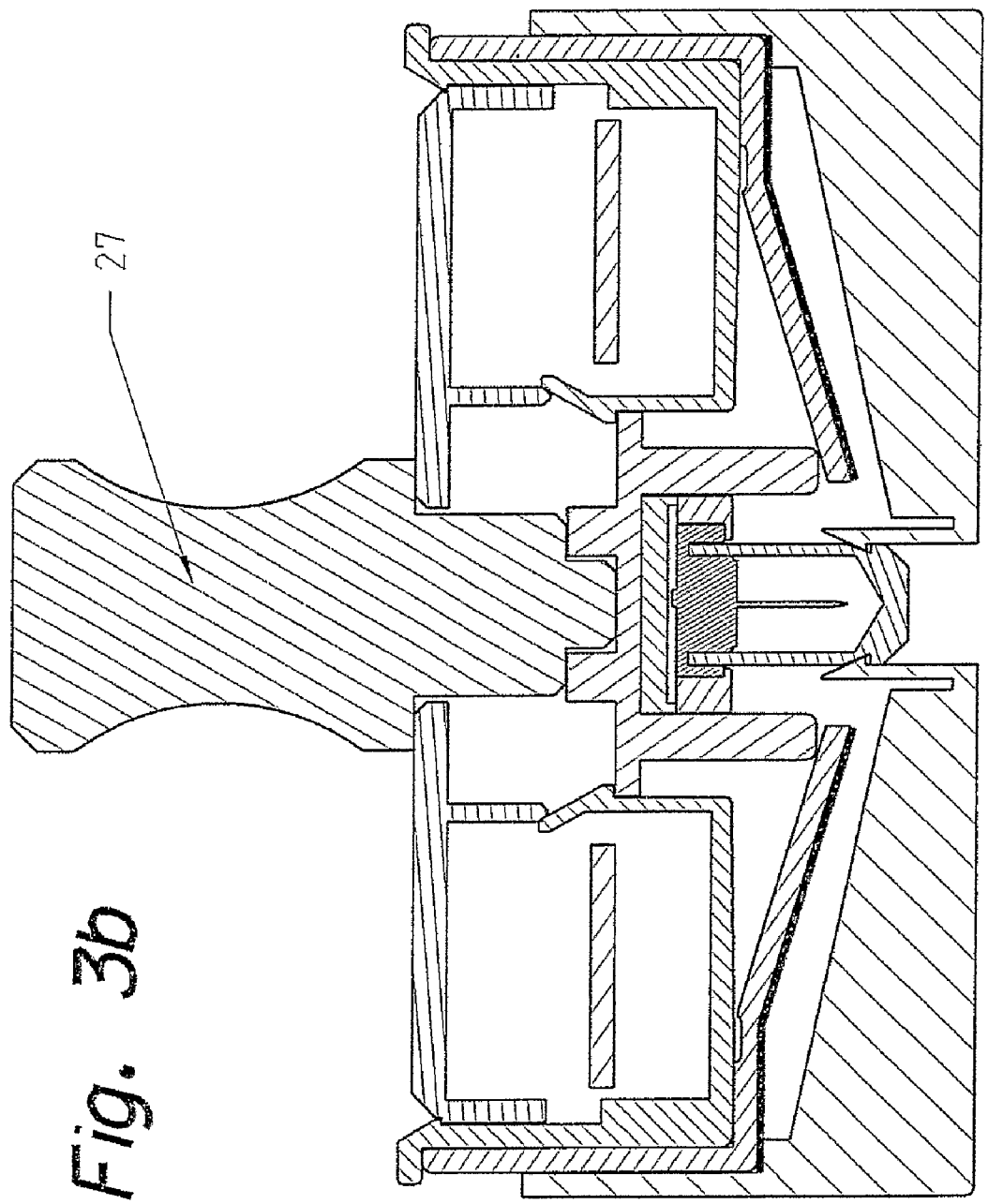
FIG. 3b shows the assembled device made ready-to-use in the tool with loaded implantation mechanism.
Figure 3C:
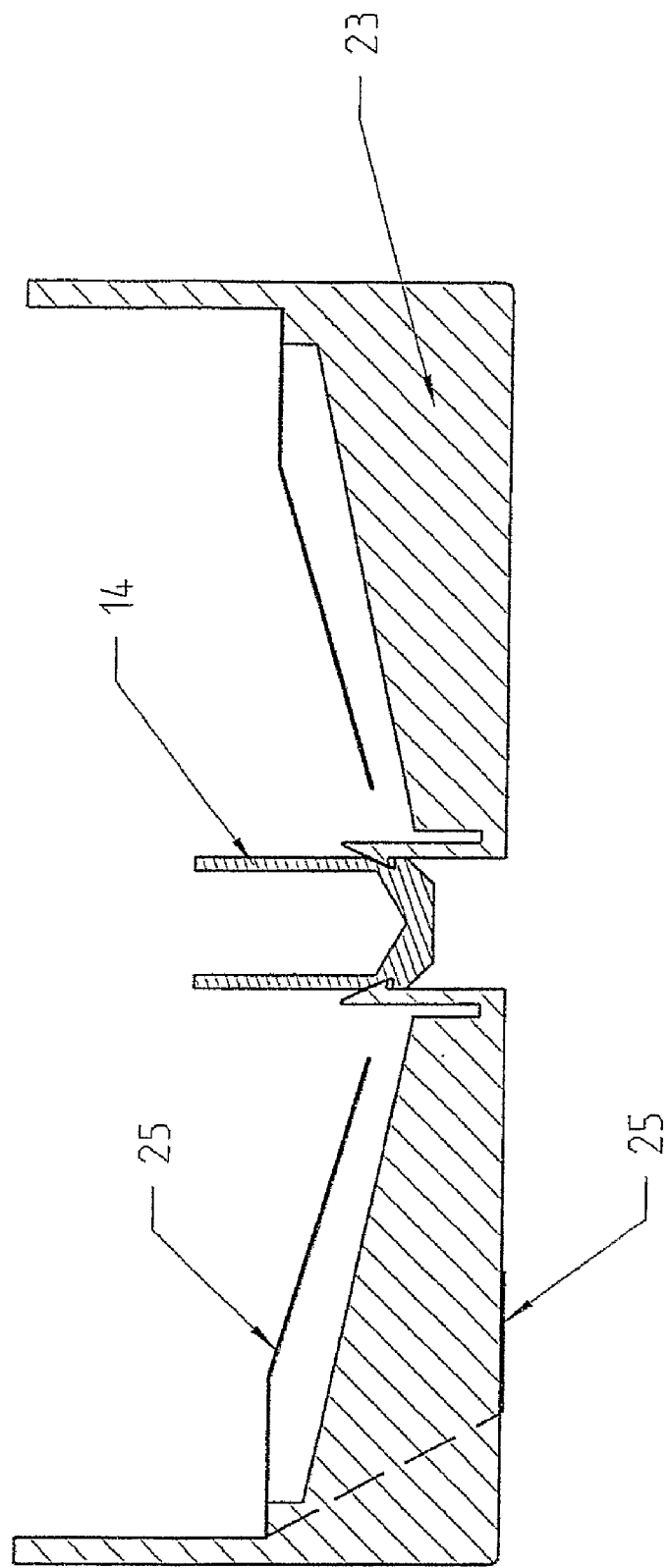
FIG. 3c shows the tool with the removed protection of the sensors and of the adhesive after the ready-to-use device has been taken out and FIG. 3d shows the ready-to-use device.
Figure 3D:
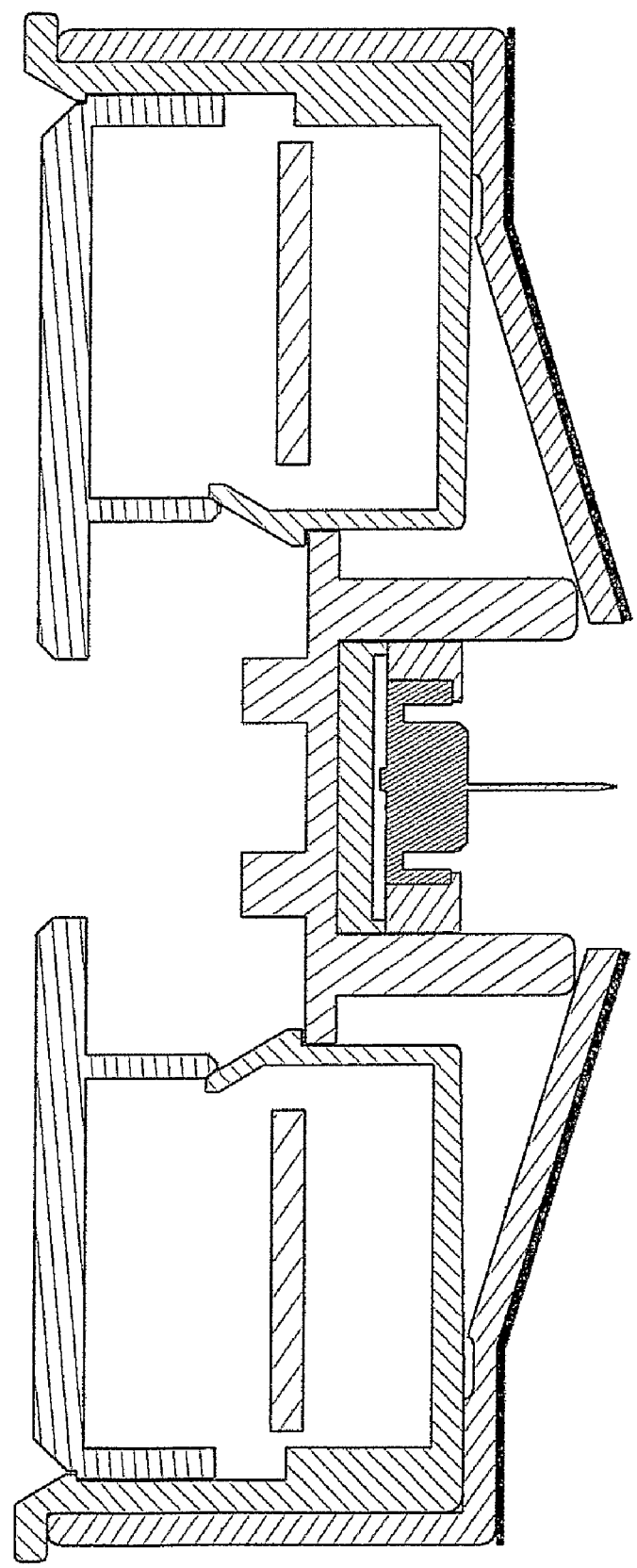

In contrast to known sensor devices, in the present inventive device the implanted parts of the sensors are inserted by thrust of a pre-stressed flexible surface which is attached to the skin by means of an adhesive layer and forms the base plate of the device. In the ready-to-use position, this flexible surface projects beyond the tips of the implantable parts of the sensors (FIG. 1b). In this position it holds the skin away from the tips when the device is placed on a suitable body area, preferably the abdomen, the thigh or the forearm, and by gentle pressing is attached by means of the adhesive layer. To insert the sensors into the skin, the base plate is released from its pre-stressed position, preferentially by pressing the cover plate of the device. This reinforces the attachment to the skin and by relaxation of the bottom plate into a flat position, the skin is moved relative to the sensors and is penetrated by the tips. It has been surprisingly found that a construction according to the present invention, preferably by a combination of a radially segmented flexible base plate with a stretchable adhesive layer, can move the skin with enough impulse that even an array of several closely spaced pins can precisely be inserted into the skin basically without sensation. A construction which allows to operate the implantation process by pressing on a release mechanism like a knob vertically to the skin surface results in even better performance since adherence to the skin and the exact geometric positioning of the implanted parts of the sensors is greatly improved as compared e.g. to a rotary movement. A great advantage of the construction according to the present invention compared to similar known devices is that all connections to the implanted parts of the sensors are rigid and no new connections have to be established after the insertion of the sensors—with known devices, such connections have to be established after the implantation of the sensors.

FIG. 1a shows a diagnostic device of this kind in section comprising a casing having a cylindrical side-wall 1 a disk-like flexible baseplate 2 in the flat position 1 of the operation mode and a cover 3 which can be moved against the baseplate and used as a release knob to start the implantation and measuring process. The baseplate has a radial segmentation, preferably into 5 to 8 segments 4 (see FIG. 1b) with a spacing between them and a central concentric opening. The segments are attached to the casing by springy hinge regions and are in addition preferentially made of a flexible material. On its underside, the baseplate has an annular adhesive layer 6 for securing the device to the patient's skin with a concentric central opening similar to the baseplate. This adhesive layer is composed of three parts, a glue 7 for fixing to the flexible baseplate, a textile 5 providing the necessary flexibility and a glue for fixing on the skin. Suitable materials with low allergenicity potential are commercially available. The adhesive layer is protected during storage with a suitable sheet. In this example, the adhesive layer 6 has the same circumference as the device but its attachment 7 to the baseplate leaves an outer zone 8 where it is not connected to the housing. The implantable parts of the sensors 9 protrude through the opening of the baseplate and during operation are inserted into the skin.

FIG. 1b shows the internal constructive elements of such a device as an explosion drawing. The flexible baseplate 2 is depicted in the pre-stressed position 2 of the ready-to-use mode. The cylindrical side-wall 1 has grooves and rectangular openings 10 serving in the attachment between the disposable and the reusable part of the device as guidance and catch mechanism. Radial bridge elements 11 attached to the side wall hold in their center an element 12 with the array of the implantable parts of the sensors. This element 12 consists of a central part 13 which fixes the sensor array in a geometrically well defined axial position, hold a removable protection cap 14 and at its upper surface provides the connections to the reusable parts of the sensors and the measuring means and provides a recognition code. The protection cap provides the necessary long-term sterility and maintains an environment which is required for a long shelf-life.

The means to position the flexible surface in two defined positions is composed in the described embodiment of two pieces, a pressure element 15 and a holding-back element 16. The pressure element 15 has a pressure plate 17 and pressure-pins 18 which press onto the segments 4 of the baseplate. The holding-back element 16 functions also as the casing of the reusable part of the device and is in a reversible way connected to the cylindrical side wall 1 which is at the same time part of the housing of the disposable part of the device. This connection is achieved guided by ribs with flexible barbs 19 which hook into the openings 10. Concentrically positioned catches 20 serve to withhold the pressure plate 17 allowing to maintain the pre-stressed position of the flexible baseplate. These catches are formed in such a way that upon pressure from the top-side by a concentric cylinder 21 attached to the inner surface of the cover 3 they bend and release the pressure plate.

The control and measuring means are fixed in the space between the bottom of the casing 16 of the reusable part and the cover 3 of the device on a support 22. The connective elements to the disposable parts of the sensors are also attached to this support (not shown in the figures).

The handling operations necessary to prepare the device ready-to-use are now described for the embodiment discussed above as example. A very important feature of the subject invention is that the connections between the implanted part of the sensors and the other parts of the device are stationary and therefore no connections have to be made manually after the implantation process. As compared to similar devices of prior art this is a big advantage for reliability, easy handling and user acceptance. This advantage is even further improved by a mounting tool which guides all necessary operations and reduces manual handling essentially to push-pull movements enabling also people with reduced level of manual skill, e.g. elderly patients with manual disablements to correctly use the device. This mounting tool allows also for easy and correct assembly and disassembly if a realization of the device is chosen with a reusable part containing all more expensive elements and a disposable part which contains the elements which should be replaced after each use such as the implanted parts of the sensors and the adhesive to the skin.

The embodiment in FIG. 2 shows schematically a solution for such a mounting tool and FIG. 3 shows the different steps of the handling process. In this example, the disposable part of the device is delivered in the disposable mounting tool according to FIG. 2a. It contains the casing with the flexible baseplate 2, the adhesive layer 6 and the implantable part of the sensor array fixed in the central part 13. A 3D representation of the mounting tool 23 is shown in FIG. 2b. It has a fixation element 24 for removing the protection cap of the sensors and one 25 (shown in FIG. 2a) for removal of the protection of the adhesive layer. The disposable part of the device is positioned and hold reversibly in the mounting tool by the groove 26. Guided by grooves 10, and corresponding ribs 19 on the reusable part of the device the reusable part can be placed only in one position into the casing of the disposable part as shown in FIG. 3a. Upon pushing down the reusable part, the two parts get assembled by a hook-mechanism (10 and 19, FIG. 1b). Loading the implantation mechanism through bringing the flexible baseplate 2 into the pre-stressed position is depicted in FIG. 3b and is accomplished by pressing a stick 27 down through the central opening of the cover 3. Alternatively, assembly of the two parts of the device and loading of the implantation mechanism can also be accomplished in one single step by a suitable coupling mechanism. Pulling out of the assembled and pre-loaded device from the mounting tool removes the protection cap 14 of the sensor tips and the protection 25 of the adhesive layer 6 as shown in FIG. 3c. The now ready-to-use device shown in FIG. 3d can be applied to the prepared skin by securing antiseptic conditions and good attachment by shaving the area if necessary. By pressing the cover the implantation mechanism is released and the measurement system actuated.

Upon termination of the measurement period, the device is removed from the skin and put back into the mounting tool. This can be done only in one pre-defined position assured by a rib and groove system 28 (see FIG. 2b). By pressing the device into the mounting tool, the disposable part gets caught by the catch of 28 irreversibly to the tool and the hooks holding the disposable and the reusable part of the device together by the system 10/19 are release by means of a rib 29 (see FIG. 2b). Pulling the disassembled reusable part of the device out of the mounting tool puts the control and measuring means back to the stand-by mode, ready for downloading of the measured data and for assembly with a new disposable part. The used disposable part caught and protected in the mounting tool is now ready for disposal.

Upon reading this specification, various alternative embodiments will become obvious to the skilled artisan. For example, the implantation mechanism could be achieved via numerous chemical, mechanical, or electrical devices. For the recognition between the disposable and reusable part of the device several mechanical, optical or magnetic codes could be used and a large variety of sensor arrays as well as control and measuring means can be accommodated with the device.

Examples of Methods for Measuring Analytes for Diagnostic Monitoring

Preferred sensors for analytes fitting well with the specifications of the subject device can be constructed following state of the art procedures for electrochemical and optical sensors. The construction of electrochemical sensors is straight-forward by coating part of the surface of the implanted part of the sensor with a suitable sensing layer, as will be described e.g. in Example 1 for glucose. For the construction of optical sensors a wide variety of methods can be optimally adapted as described in the following for direct determination of the analyte or for indirect monitoring using suitable indicators. Such general methods can be coupled to analyte-specific enzyme reactions or to specific binding to receptors or antibodies.

Optical Systems and Direct Determination of Analytes

It is well known from the literature that clinically relevant analytes such as glucose, alcohol, urea, creatinine etc. can be determined directly by taking NIR, IR or Raman spectra from body fluids (serum, blood, salvia urine etc) and by using statistical techniques such as PLS or PCA or neural networks for evaluation. Many optical arrangements have been claimed in the past for measuring clinical parameters through the finger, the tongue or ear. A disadvantage of these arrangements is that radiation has to cross the skin which shows a large spectroscopic variance not only from individual to individual but can change its spectroscopic properties also for a single individual within a day. The arrangement suggested herein has the advantage that measurements are performed within the tissue using the subject device.

As depicted in FIG. 4a, a preferred arrangement consists of one (or several) central light transmitting fibre(s) 30 that transmit light from the light source 31 to the subcutaneous tissue. An efficient coupling-out of light from this optically isolated fibre 32 can be achieved by introducing refractive index inhomogeneity into the terminal part of the stripped fibre which act as efficient light scatters 33. Alternatively specially tapped fiber tips can be prepared with optimized geometries for the in- and out-coupling of light. This central fibre 30 which transmits the light to the tissue to be analyzed is surrounded by several fibres 34 which have the ability to couple-in and transmit back to a detector 35 light that is emitted from the central fibre. The light emerging from these fibres can pass a filter in order to allow monitoring optical density at different wave lengths. The light assembling fibres should have different distance from the central one in order to allow measurements over different optical path length. To cope for differences in light scattering by the tissue special modulation techniques as described for instance by G. Spanner et al. (Fresenius, J. Anal. Chem. 1996, 354, 306) can be applied.

Optical Enzyme Sensors Based on Monitoring Fluorescence or Absorption of Indicators Optical enzyme sensors are based on the fact that an enzymatic reaction in general not only changes the concentration of its substrate but changes also the concentration of molecules such as $O_2$, $H_3O^+$ or $CO_2$ that are produced or consumed by the enzymatic reaction. A concentration change of such molecules can easily be followed using absorbing or fluorescing molecules, so called indicators that change their absorption or fluorescence behaviour specifically with the concentration change of above mentioned molecules. In a fibre optical enzyme sensor the reaction phase with enzyme and indicator is fixed to an optical fibre that transmits light from the light source to the reaction phase and back to a detector as described by E. A. H. Hall (Biosensoren, Springer Verlag Berlin, 1995, 351 ff).

Several fiber optical arrangements to follow changes in the concentration of small molecules in a reaction phase containing enzyme and indicator are depicted in FIG. 4b. A bifurcated fibre arrangement can be used to transmit light from a light source 31 to the immobilized reagent phase and back to a detector 35. The reagent phase can then consist of a porous tube of approximately 1-2 mm length which serves to hold the reagents (enzyme, indicator) in place. The porous tube 36 should be chosen to allow analyte molecule to penetrate into the reagent phase but can also act as a filter membrane to separate the analyte molecule from other components of body fluids which could interfere with the enzymatic reaction or which could influence absorption and fluorescence behaviour of the indicator. A cap 37 at the end of the porous tube blocks the incident light from directly interacting with the sample avoiding a potential source of interference. In case of a homogeneous phase between fibre end and cap the cap can also act as a reflector to bounce light back into that fibre 34 which transmits light back to the detector. However, the compartment between fibre end and cap can also contain solid particles, which serve on one hand as a solid phase to immobilize enzymes and indicators and on the other hand as light scatters for the incident radiation so that some of it is redirected into the fibre transmitting light to the detector.

A similar arrangement can also be realized with a single fibre 38. Incident and light transmitted to the detector are then separated at the end of the light transmitting fibre by a semi permeable mirror 39.

Alternatively, an optical fibre can also be stripped off from the optical isolation 40. The reaction phase 41 can then be mounted directly to this part of the fibre. The incident light interacts with the indicator molecules in the reaction phase via the evanescent field to monitor changes in absorption and to excite fluorescence. Emitted light from the fluorophores is analogously coupled into this fibre 38 again via this evanescent field. This evanescent field could be enhanced by covering the surface of the stripped fibre with a thin gold layer. Within this gold layer, a so called surface plasmon could be excited. The electromagnetic field of this evanescent field is by orders of magnitude stronger then the electromagnetic field of the evanescent field of a non covered optical fibre. This surface plasmon effect can therefore be explored to monitor absorption changes more sensitively and to excite more efficiently the fluorescence of fluorophores immobilized within the penetration depth of that evanescent field.

By-products of enzymatic reactions such as $H_3O^+$, $O_2$ or $CO_2$ or $NH_3$ can be measured using the following reaction phases:

pH sensors can be constructed by immobilizing pH indicators on the surface. A prerequisite of such indicators is that they have a pKa close to the relevant pH range of the analysis matrix. An indicator that has been used by J. Peterson et al. (Anal. Chem. 1980, 52, 864) is phenol red with a pKa of 7.6. It was demonstrated that such sensors work in the physiological range from 7.4-7.0 with a resolution of 0.01 pH units.

Immobilizing pH sensitive fluorophores is another possibility. Such fluorescence indicators change with pH either the wavelength of excitation or the wavelength of emission. D. W. Lüebbers et al. uses methylumbeliferon (Z. Naturforsch., C: Biol. 1975, 30c, 532) whereas Wolfbeis (Anal. Chem. 1983, 314, 119) takes 8-hydroxy-1,3,6-pyrenetrisulfonic acid. Fluorescein and its derivatives can also be used as fluorimetric pH indicators as demonstrated by Milanovitch (Proc. SPIE-Int. Soc. Opt. Engl. 1984, 494, 18).

Most optical $O_2$ sensors reported to date are based on fluorescence quenching. Linear calibration curves can be obtained by plotting the fluorescence intensity in the absence of $O_2$ versus the intensity of $O_2$ at a given oxygen pressure. A variety of reagent phases have been used in optical oxygen sensors, such as pyrenebutyric acid immobilized on solid substrate or perylenebutyrate.

A blood $NH_3$-optical sensor is described by Smock et al. (Anal. Chem. 1979, 51, 505). The reaction phase consists of a polymer matrix which contains ninhydrin. The optical change is based on the formation of the characteristic Ruhemann Purple colour in the presence of $NH_3$.

Any of the above described optical sensors can be modified for monitoring clinically relevant parameters. The modification includes immobilization of a suitable enzyme within the reaction phase. The substrate of the immobilized enzyme represents the analyte molecule to be monitored. The enzyme acting on the substrate changes the concentration of the chemical parameter for which the optical measurement is sensitive (for instance $O_2$, pH, $CO_2$ etc.). Numerous such enzymes have been suggested in the literature (in Biosensors, Fundamentals and Applications, A. P. F. Turner et al eds, Oxford Sci Publ. 1987 pp. 135). The most prominent one is Glucose Oxidase which catalyzes the reaction from glucose to gluconic acid whereby the $O_2$ and the pH are changed in the reaction phase. By coupling this enzyme to a pH- or $O_2$-optode enables monitoring of glucose in biological fluids as demonstrated by N. Uwira et al. (Adv. Exp. Med. Biol 1984, 169, 913). The catalytic transformation of penicillin to penicillin acid is accompanied by a change in pH which can be monitored by a pH-optode when the enzyme is coupled to the reactive phase containing fluorescein as an indicator as described by O. S. Wolfbeis et al. (Anal. Chem. 1988, 332, 255).

Figure 4C:
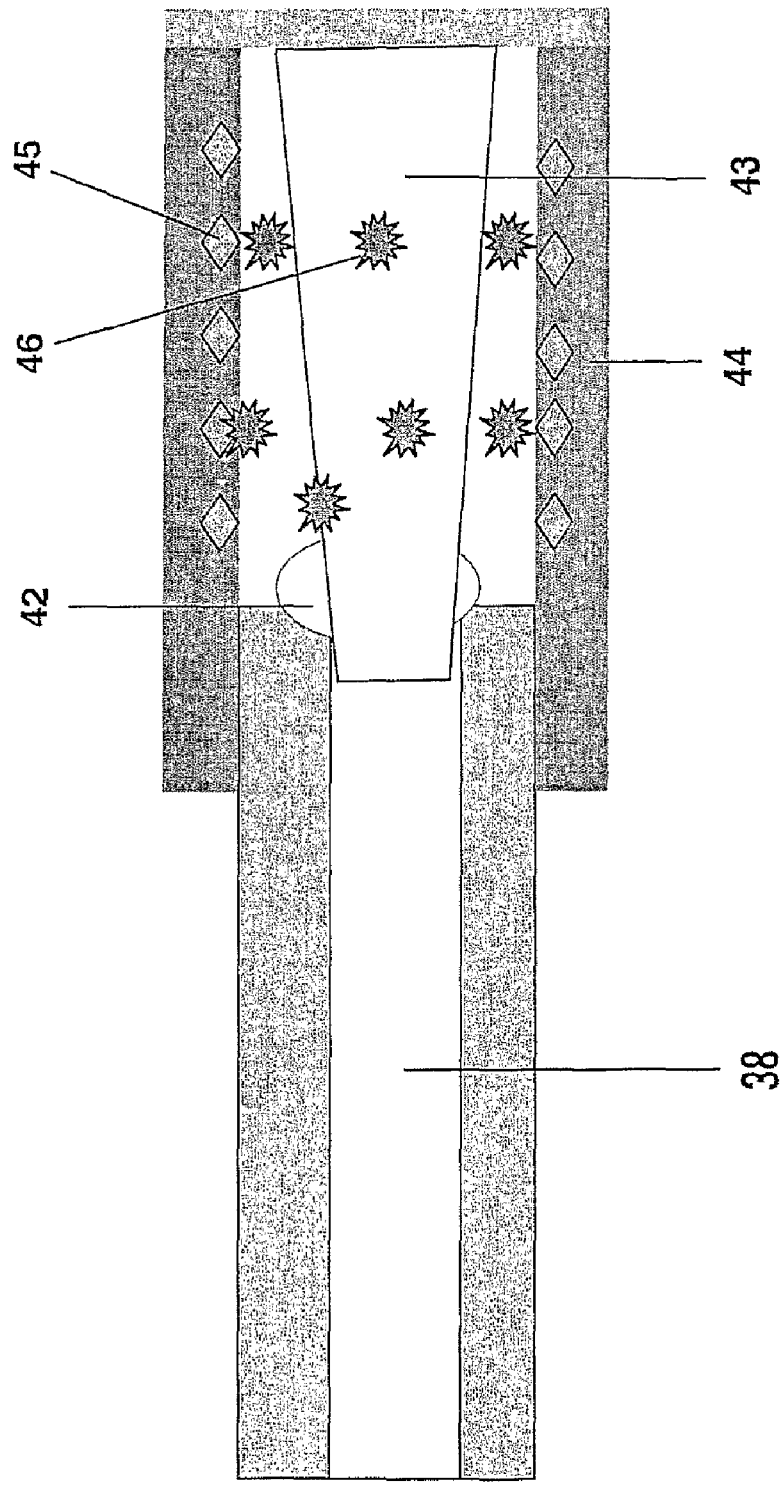

Optical Biosensors Based on the Use of Immobilized Receptor or Binding Molecules Such sensors can be designed for several analytes like e.g. glucose. A general device fulfilling these requirements is depicted in FIG. 4c. Such a device needs an optically isolated fibre 38 with an aperture 42 that illuminates as a light cone 43 only the inner part of the reagent phase and not the porous membrane 44 where receptor molecules 45 are immobilized. A ligand 46 of the receptor which cannot penetrate the porous membrane and which is labelled by a fluorescent label is incorporated into the inner compartment of the reagent phase. In the absence of any competing ligand the labelled ligand binds to the receptor molecule immobilized on the porous membrane. Intensity of fluorescence light is small because due to the small aperture of the fibre the incident light can not excite the fluorescent labels bound to the receptors. If however competing non fluorescent labelled ligand (the analyte) diffuses into the reagent phase and displaces the labelled ligand, the concentration of labelled ligand in the illuminated volume increases and so does the fluorescence intensity.

A sensor working along this principle has been described by F. F. Bier et al. (Sensors and Actuators 1992, 7, 509) for measuring glucose concentration. Concanavalin A serves as the receptor. Dextran labelled with fluorescein represents the labelled macromolecular ligand that binds to the receptor but does not penetrate the porous membrane. Glucose is the analyte which competes with dextran for the binding sites on concanavalin A. At equilibrium, the level of free fluorescein labelled dextran is measured and is correlated to the external glucose concentration.

The invention will be further characterized by the following examples. These examples are not meant to limit the scope of the invention which has been set forth in the foregoing description. Variations within the concepts of the invention are apparent to those skilled in the art.

Example 1

Device for Measurement of the Concentration of Glucose in Subcutaneous Interstitial Fluid Over 1 to 3 Days The device according to the preferred embodiment as described above was equipped with an array of seven implantable electrodes of 150 μm diameter and 4 mm implantable length. The arrangement of the electrode array is shown in FIG. 5. Four electrodes were coated with a glucose sensing layer, as described below, two at an injection depth of 3.0 mm 47 and two of 2.0 mm 48. Two electrodes served as Ag/AgCl reference 49 and the central electrode was a Pt counter-electrode 50. This arrangement results in several advantages as compared to implantable sensors described in prior art which all contribute to superior reliability concerning the accuracy of the glucose level determined. The well defined geometric arrangement of the implanted electrodes allows to separate sensing electrode and counter-electrode as different pins and allows therewith to optimize by miniaturization for minimal invasiveness with, at the same time, a sufficiently large surface for the sensing layer. First, a larger sensing layer improves measurement signal level and stability. Second, one of the biggest problems in achieving reliable measurements of glucose over prolonged time in subcutaneous interstitial fluid is the influence of the body reaction to injury fouling the sensor. Minimal invasiveness minimizes these reactions. In addition, the use of several glucose sensors depicted in FIG. 5c in parallel and at different insertion depth allows to correct the glucose determination over time. The response of the individual sensors can first be adjusted against each other and later the highest signal achieved can be used since reaction to injury always decreases the signal and is a partly random process. Alternatively, one or several sensors in the array can be used to monitor endogenous substances with a low level of diurnal variation like e.g. citrate and used for correction of sensor fouling over time.

The pin-like implantable part of the glucose sensors depicted in FIG. 5c is made of stainless steel 51 and has an electrolytically prepared sharp point at the tip and a circular recess of 0.03 mm depth and 1 mm width on the shaft, with the center of the recess 1.0 or 2.0 mm from the tip. After cathodic activation to remove the oxide film from the surface, the stainless steel is coated with rhodium 52 by galvanostatic electrodeposition under constant current ($50 A/m^2$). The surface outside, except the recess area, was insulated with a polyimide layer 53. The recess area was coated with a glucose sensing layer essentially following the description by Wagner et al (Proc. Natl. Acad. Sci. 1998, 95: 6379-6382). It was built up of a wired enzyme sensing layer 54, a mass transport controlling membrane 55 and covered by a biocompatible polyethylene oxide film 56.

The "wired" enzyme sensing layer was formed by crosslinking glucose oxidase to poly[(1-vinylimidazole)osmium(4,4'-dimethylbipyridine)$_2$Cl] via poly(ethylene glycol) diclycidyl ether 400 (Polysciences). The glucose flux restricting layer was formed by sequentially filling the recess and curing twice with 1% solution of cellulose acetate in cyclohexanone; once with a 0.5% solution of Nafion (Aldrich) in n-propanol; and once with a freshly prepared solution of poly(vinylpyridine) acetate (25 mg/ml in water) and polyfunctional aziridine (XAMA-7, E.I.T., Lakewillie, S.C.) (30 mg/ml in water) in a 1:2 volume ratio.

All glucose sensors are connected to an amperometric system via multiplexing and operated as working electrodes in connection with the Pt counter and the Ag/AgCl reference electrodes preferentially at a low operating potential of −0.1 V. The signals are processed every two minutes into calculated glucose concentrations. These values are stored in the memory of the in-built microprocessor for off-line downloading and computer analysis and are in parallel transmitted wireless to a wrist-watch which converts the signals into a colour-coded signal message through an LCD dial plate for averting the patient about his actual glucose status and the trend of changes. Alternatively, this wireless transmitted signal can be used as a control element for an insulin infusion pump.

Other endogenous analytes, like lactate, urea, creatinine etc but also drugs and xenobiotics like alcohol can easily be measured using the same principles with appropriate selective enzymes.

Example 2

Inulin Clearance to Assess Renal Function

As an example, the use of antibiotics can largely be improved esp. in life-threatening conditions by dose-adjustment according to renal function. Success of treatment in severe nosocomial infections is often a question of finding the optimal individualized dosage resulting in high enough plasma levels over sufficient time to kill the pathogens (time over MIC). On the other hand, severe dose-dependent side effects can result due to over-dosage. The severity of the clinical condition and the use of several antibiotics and other drugs in parallel make the choice of the optimal dosage even more problematic. The results of a recent trial of the University of Milan (F. Scaglione, $8^{th}$ ISAP Symposium, 2002) demonstrated that adjustment of antibiotic treatment in such a condition according to renal clearance could halve the failure rate and of the mortalities (from 10% to 5%) and shorten the length of hospitalization by one third. There are no convenient methods available to determine renal clearance at the bed-side. Serial blood samplings and relatively complicated laboratory analysis prevent the routine application of the creatinine or the inulin clearance test for renal function.

The inulin clearance test is the gold standard for assessing glomerular filtration rate and can be measured after a single bolus injection of 5 g of inulin by following the disappearance over several hours (K. Jung et al. Clin. Chem. 1992, 38, 403-407). Inulin readily equilibrates to the interstitial fluid and therefore its excretion can be readily followed with the subcutaneous diagnostic device of the subject invention.

The sensor for determination of inulin concentration over time was constructed essentially in the same manner as outlined above for glucose in Example 1. The selective electrochemical determination of inulin made use of a two-step enzymatic reaction, first the hydrolysis of inulin via inulinase as described by Kuehnle et al (Nephron 1992; 62: 104-107) followed by amperometric determination of fructose using the enzyme fructose dehydrogenase and the mediator tetrathiafulvalene co-immobilized by cross-linking with glutaraldehyde following the procedure described by S. Capuzano et al (Anal. Bioanal. Chem. 2003; 377: 600-607). The incorporation of sensors with the same construction but omitting inulinase into the array allows for correction of the measured values for unspecific signals.

The sensitivity of the electrode can be further improved by increasing the sensing layer by means such as fluted or dent shaft, nanotubes, porous anorganic or organic coatings or polymers.

In one embodiment for convenient bedside use the cap of the device was constructed in such a way that it incorporated a LCD display showing the calculated clearance in mL/min and the corresponding recommended dose of the selected antibiotics in % of the standard dose chosen by the physician assuming normal renal function. A microprocessor in the device can be loaded with recommended values for a variety of antibiotics and the antibiotics in actual use can be called up onto the display. It is obvious that many variations according to convenience of application of the device are possible.

The example above describes only one of many possible applications. Determination of renal function based on the clearance of inulin or using alternative sensors for creatinine, p-aminohippuric acid or other clinically well established substances can be very important for the correct dosing also of other drugs and for diagnostic purposes.

Example 3

Pharmacokinetics of Drugs to Guide Choice of Best Treatment Alternative and Dosing Schedule Adverse drug reactions were conservatively estimated to account for as many as 2.2 million hospital events, and as many as 100,000 deaths a year in the US alone (Pomeranz, JAMA 1998; 279: 1216-1217). An important cause of such adverse drug reactions is caused by inadequate individual dosing due to large variations in the pharmacokinetics of the drugs in different individuals. The reasons for such variations are partly the genetic makeup but also environmental factors, the general condition and concomitant drug treatments of a patient play an important role. For many drugs such unpredictable variations even among normal individuals result in standard deviation in the values observed for the main pharmacokinetic descriptors F, CL and Vss of about 20%, 50% and 30% respectively. This means that 95% of the time the plasma concentration that is achieved with a standard dose will be between 35% and 270% of the target; this is an unacceptably wide range for a drug with a low therapeutic index. The variation in a population with various illnesses and concomitant drug treatments can be even more pronounced.

Of particular interest in this context are drugs with a narrow therapeutic window like e.g. the blood thinner warfarin and indications in which the efficacy of the drug becomes apparent only after prolonged treatment of several weeks like antidepressants and antipsychotic drugs.

As an example a diagnostic device for the simultaneous determination of the pharmacokinetics of 3 frequently used antidepressants fluoxetin, paroxetin and venlafaxine given at sub-therapeutic dose is described.

The sensors for the three drugs were constructed as optical sensors essentially following the design depicted in FIG. 4c and described by S. Mansouri and J. S. Schultz (Biotechnology 1984, 2: 885). Monoclonal antibodies were prepared against albumin-drug conjugates serving as haptens and selected for high affinity for the parent drug and somewhat lower affinity for the conjugate in order to increase the sensitivity of the sensors. The antibodies were immobilized on the inside wall of a Cuprophan dialysis fiber (Enka, Wuppertal, Germany), constituting 1 mm of the implanted part of the sensor. The conjugates were labeled with FITC and introduced into the porous fiber chamber at a concentration which was almost totally bound by the immobilized antibody. The optical system used a laser diode as light source and commercially available miniaturized components. The entire optical system and the electronics were placed into the reusable part of the device and the optical coupling with the disposable part was achieved through a single optical fiber.

Various modifications and changes may be made without departing from the spirit and scope of the invention. For instance, larger molecular weight substances like hormones such as insulin or other proteins can be preferably monitored with sensors using the principle of surface plasmon resonance.

It is obvious that besides the electrochemical principles described for sensors in examples 1 and 2, the optical principles described above, especially in combination with established technologies such as immunodetection, electrochemoluminiscence can form a common detection platform, which greatly facilitates the design and construction of devices according to the subject invention, and allow the determination of several analytes in parallel with sensors of different selectivities. With such a design and the selection of panels of xenobiotics/drugs which are proven to be safe if administered to patients at low dosage for diagnostic purposes and span the involvement of several metabolic pathways for their elimination, a phenotypic profiling of an individual patient at a given time can be achieved. Examples of such compounds are i.a. xanthin, coffein or antipyrin, which results in 3 different metabolites, depending on the individuals P450 isozyme pattern and which can be measured in parallel using the subject sensor device. Such a phenotyping gives a global picture of the individuals drug metabolizing capacity, covers also, but is not restricted to, the important hepatic metabolic functions, e.g. the interplay of the P450 isozymes which can show wide interindividual variations due to the genotype but also due to acquired individual factors such as life style, disease history, concomitant medications, alcohol consumption and other environmental factors. The necessary actual in vivo data from an individual can be conveniently obtained with suitable diagnostic devices according to the subject invention. The data can be downloaded to a diagnostics information system using state-of-the art transmission tools, well established through internet and telecommunication, for further processing. Using advanced algorithms like physiology based pharmacokinetic modeling together with diagnostic data of the patient, such as e.g. age, body mass index, drug treatments allows to provide the physician with relevant information for an individualized drug treatment and optimized dosing schedule. Additional information e.g. of renal function and genomic profiling can further improve the predictions.

The invention has been described with reference to a few specific and preferred embodiments, techniques and applications. However, it will be apparent to one of ordinary skill in the art that many variations and modifications and adaptations to special applications and needs can be made while remaining within the spirit and scope of the invention.

The invention claimed is:

1. Device for the in-vivo measurement of the concentration of an analyte in a body fluid comprising: a) a component with a flexible surface, b) means for securing adherence of that surface to the skin, c) a rigid part holding one or more subcutaneously implantable sensors, d) means for positioning the flexible surface relative to the sensors in such a way that in a first position the sensors are concealed by the surface and in a second position implantable parts of the sensors are exposed above the surface, and e) a releasable mechanism that when locked retains the means for positioning at the first position such that the surface deforms to a convex shape and when released permits the surface to move the means for positioning to the second position while inserting the implantable parts of the sensors into the skin.

2. Device according to claim 1, wherein a control and measuring means are integrated.

3. Device according to claim 1, where the implantable part of a sensor is a full, rigid, thin pin-shaped module.

4. Device according to claim 1, where the implantable part of a sensor has a diameter below 250 μm and an implantation depth of 1 to 5 mm.

5. Device according to claim 1, where the implantable part of a sensor is a pin coated with a sensing layer.

6. Device according to claim 1, where the implantable part of a sensor includes a probe serving as a semi-permeable interface between the body fluid and the sensing layer.

7. Device according to claim 1, where the implantable part of a sensor includes a light conducting element.

8. Device according to claim 1, where the implantable part of a sensor is a ion-selective probe.

9. Device according to claim 1, where the implantable part of a sensor is a sonnar probe.

10. Device according to claim 1, where the implantable part of a sensor is a surface plasmon resonance probe.

11. Device according to claim 1, where the implantable part of the sensors has a structured surface in such a way that the exposed surface of the sensing layer is increased and protected from stripping during insertion into the skin.

12. Device according to claim 1, where several sensors are used each being selective for a specific analyte.

13. Device according to claim 1, where the means for securing adherence to the skin is an adhesive layer for temporary wearing on the body, and the adhesive layer is fixed on the flexible surface of the device by a reduced surface in comparison to the adhesive surface to the skin.

14. Device according to claim 1, where the releasable mechanism is configured to bring the flexible surface into two distinct positions relative to the implantable tip of the sensors using the flexibility of this surface based on a rapid movement from the first to the second position by relaxation from an enforced tense position.

15. Device according to claim 1, where the releasable mechanism is actuated by pressing a knob or the cap of the device.

16. Device according to claim 1, where control and measuring means a) survey the correct functioning of the device, b) transform sensor signals into analyte measurements, c) store, display and transmit analyte measurements online or batch-wise, and d) give warning signals if analyte measurement is not within a predefined rang.

17. Device according to claim 1, where the device is composed of a reusable part comprising all control elements and a disposable part comprising at least the elements for adhesion to the skin and insertion into the skin.

18. Device according to claim 17, where the reusable part can be combined with a variety of disposable parts with different sensors and there is an automatic recognition by means of a code on the disposable part.

19. Device according to claim 17, where the disposable part is housed in a tool which allows, essentially through push-pull manipulations the assembly with the reusable part as well as all operations for making the device ready-to-use, and after use to disassemble the two parts.

20. Method for measuring the concentration-time profiles of endogenous substances over a prolonged time period from hours to several days, by a) preparing the device according to claim 1, ready-to-use, b) attaching it to the prepared skin of a subject, c) releasing the mechanism to insert the implantable parts of the sensors into the skin and to start a measuring process, d) measuring the concentration of the analytes by means of processing sensor signals.

21. Method for measuring the concentration-time profiles of exogenous substances including drugs and their metabolites or model compounds with well-established metabolic pathways over a prolonged time period from hours to several days, comprising a) preparing the device according to claim 1 ready-to-use, b) attaching it to prepared skin of a subject, c) releasing the mechanism to insert the implantable parts of the sensors into the skin and to start a measuring process, d) measuring the concentration of one or more drugs or metabolites by means of processing sensor signals, and e) administering one or more substances to the subject by oral, intravenous, subcutaneous or other means as an acute, subchronic or chronic application.

22. The method of claim 20 or 21, further comprising using the measured concentrations for the diagnosis of organ function.

23. The method of claim 20 or 21, further comprising using the measured concentrations for the individualized adjustment of drug dosing and prediction of drug-drug interactions.

24. The method of claim 20 or 21, further comprising using the measured concentrations, personal diagnostic data of the patient and pharmacokinetic modeling algorithms to select a drug dosing schedule.

25. The method according to claim 20 or 21, comprising receiving a signal from an electronic sensor in said device and using said signal to automatically adjust the dosing of pharmacologically active compounds being delivered to the subject by infusion pumps.

26. The method according to claim 20 or 21, comprising receiving a signal from an electronic sensor in said device and using said signal to automatically adjust insulin injection and/or oral anti-diabetic drug treatment for the subject.

* * * * *